(12) United States Patent
Nishio

(10) Patent No.: US 11,525,476 B2
(45) Date of Patent: Dec. 13, 2022

(54) BEARING AND MEDICAL DEVICE

(71) Applicant: TERUMO KABUSHIKI KAISHA, Tokyo (JP)

(72) Inventor: Kosuke Nishio, Machida (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 380 days.

(21) Appl. No.: 16/800,455

(22) Filed: Feb. 25, 2020

(65) Prior Publication Data

US 2020/0191196 A1 Jun. 18, 2020

Related U.S. Application Data

(63) Continuation of application No. PCT/JP2018/031816, filed on Aug. 28, 2018.

(30) Foreign Application Priority Data

Sep. 5, 2017 (JP) .............................. JP2017-170142

(51) Int. Cl.
*F16C 19/06* (2006.01)
*F16C 33/58* (2006.01)
(Continued)

(52) U.S. Cl.
CPC ........ *F16C 19/06* (2013.01); *A61B 17/32002* (2013.01); *F16C 19/507* (2013.01);
(Continued)

(58) Field of Classification Search
CPC ...... F16C 19/06; F16C 19/507; F16C 33/585; F16C 2316/10; A61B 17/32002;
(Continued)

(56) References Cited

U.S. PATENT DOCUMENTS 754,436 A * 3/1904 Duncombe ......... F16C 33/3713
384/522
2,983,557 A 5/1961 William
(Continued)

FOREIGN PATENT DOCUMENTS

AU 2013205920 A1 * 6/2013 ......... A61B 1/00087
JP 2508178 B2 6/1996
(Continued)

OTHER PUBLICATIONS

International Search Report (PCT/ISA/210) and translation and Written Opinion (PCT/ISA/237) dated Nov. 27, 2018, by the Japanese Patent Office as the International Searching Authority for International Application No. PCT/JP2018/031816.
(Continued)

*Primary Examiner* — Phillip A Johnson
(74) *Attorney, Agent, or Firm* — Buchanan Ingersoll & Rooney PC

(57) ABSTRACT

Provided are a bearing and a medical device in which a gap is secured between an inner ring and an outer ring, and the gap can be used as a flow path for a fluid or an object. A bearing having a plurality of rolling elements between an inner ring and an outer ring is provided with a raceway surface on which the rolling elements roll on the outer ring and receiving portions for rotatably accommodating the rolling elements at a position of the inner ring facing the raceway surface.

20 Claims, 10 Drawing Sheets

(51) Int. Cl.
  *A61B 17/32* (2006.01)
  *F16C 19/50* (2006.01)
(52) U.S. Cl.
  CPC ...... *F16C 33/585* (2013.01); *A61B 2217/007* (2013.01); *F16C 2316/10* (2013.01)
(58) Field of Classification Search
  CPC .. A61B 17/320758; A61B 2018/00202; A61B 2217/007
  See application file for complete search history.

(56) References Cited

U.S. PATENT DOCUMENTS

| | | | | |
|---|---|---|---|---|
| 5,287,845 A | * | 2/1994 | Faul | A61B 1/12 600/156 |
| 5,405,348 A | | 4/1995 | Anspach et al. | |
| 5,855,439 A | * | 1/1999 | Bonitz | F16C 33/3812 384/614 |
| 5,925,055 A | * | 7/1999 | Adrian | A61B 17/2202 606/171 |
| 6,033,408 A | * | 3/2000 | Gage | A61B 17/1633 173/218 |
| 6,209,886 B1 | * | 4/2001 | Estes | B23B 51/126 279/143 |
| 6,562,055 B2 | * | 5/2003 | Walen | A61B 17/32002 606/167 |

FOREIGN PATENT DOCUMENTS

| | | |
|---|---|---|
| JP | H09303407 A | 11/1997 |
| JP | 2002005179 A | 1/2002 |
| JP | 2005328971 A | 12/2005 |
| JP | 2007263204 A | 10/2007 |
| JP | 2015511144 A | 4/2015 |

OTHER PUBLICATIONS

An English Translation of the International Search Report (Form PCT/ISA/210) and the Written Opinion of the International Searching Authority (Form PCT/ISA/237) dated Nov. 27, 2018, by the Japan Patent Office in corresponding International Application No. PCT/JP2018/031816. (8 pages).

\* cited by examiner

FIG.1
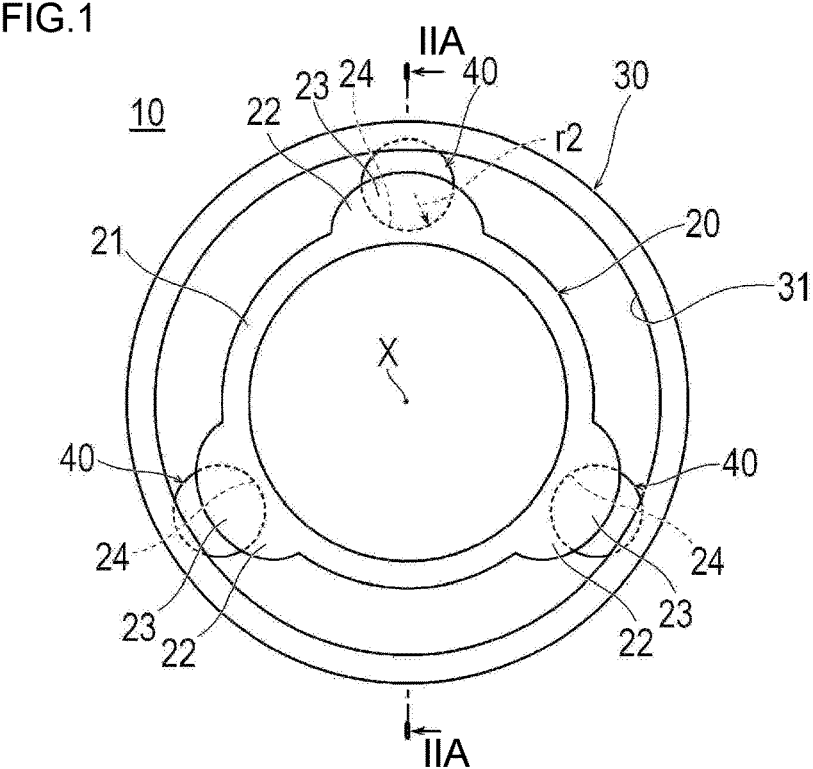
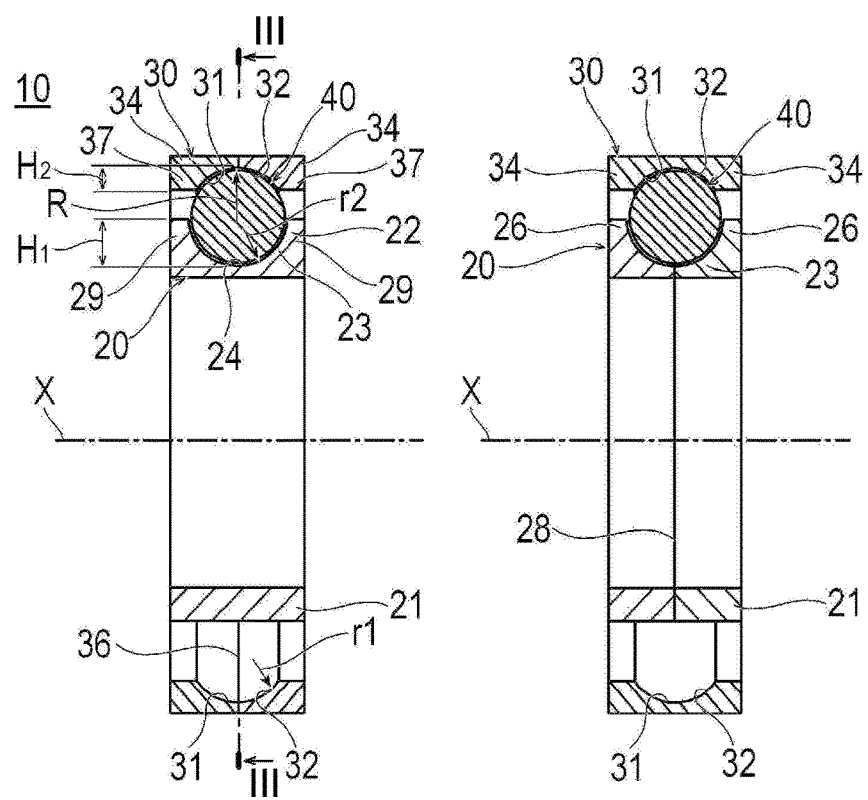
FIG. 2(A)          FIG. 2(B)

FIG. 3
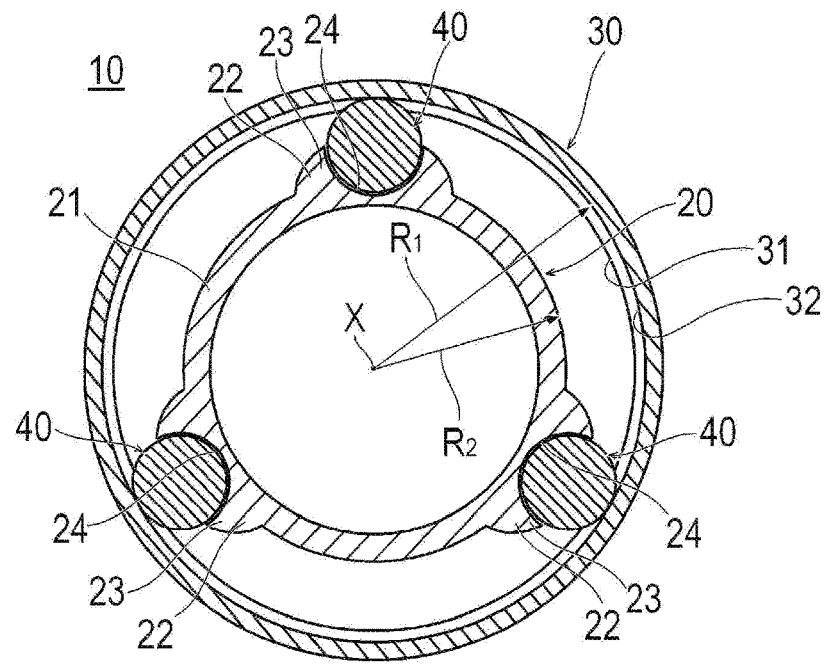
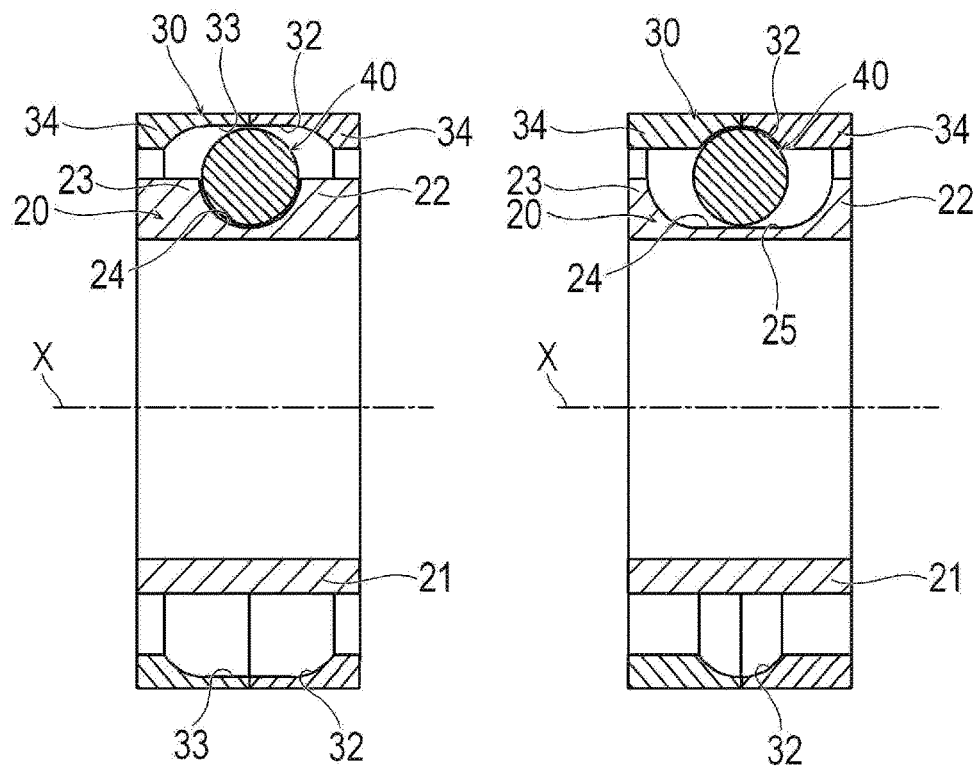
FIG. 4(A)　　　　　FIG. 4(B)

FIG. 5
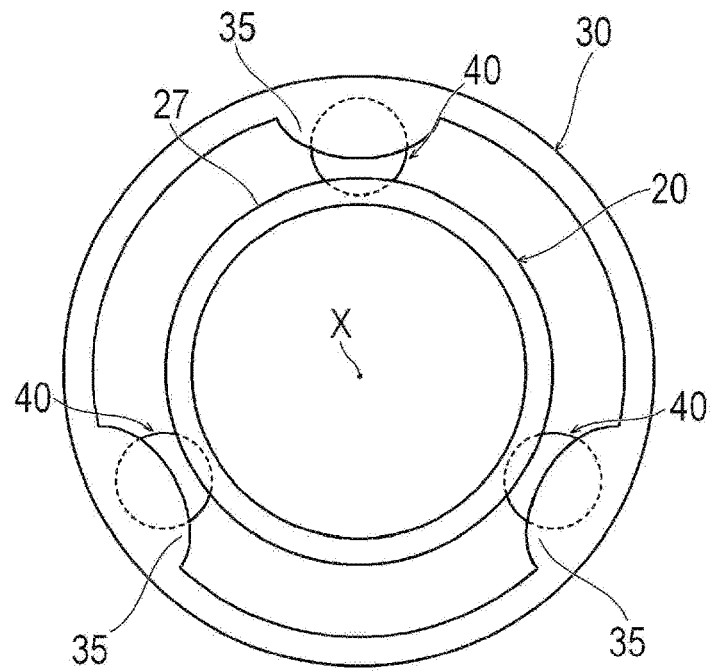
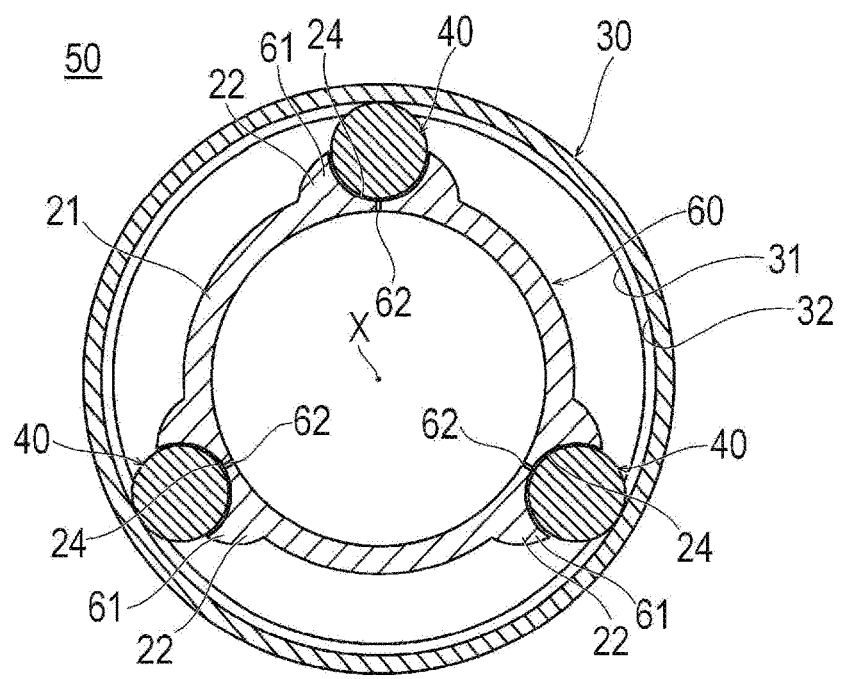
FIG. 6

FIG. 11
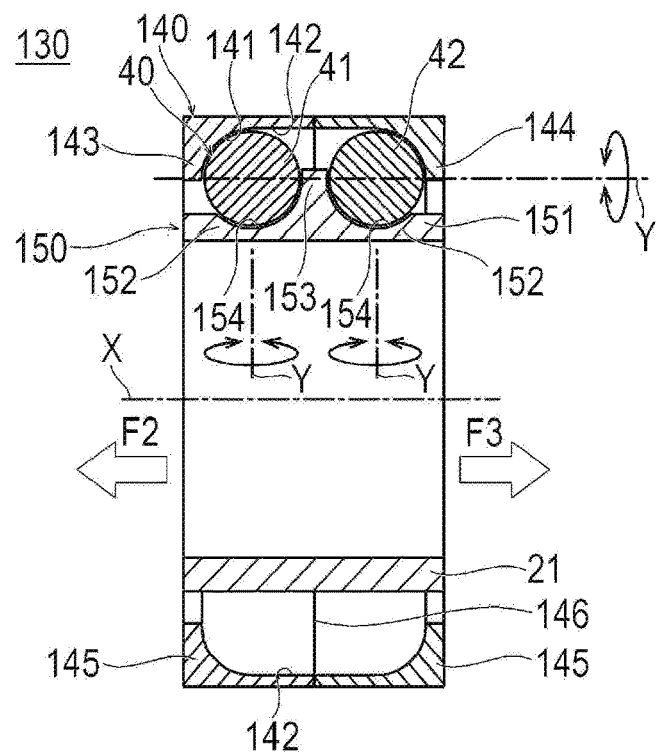
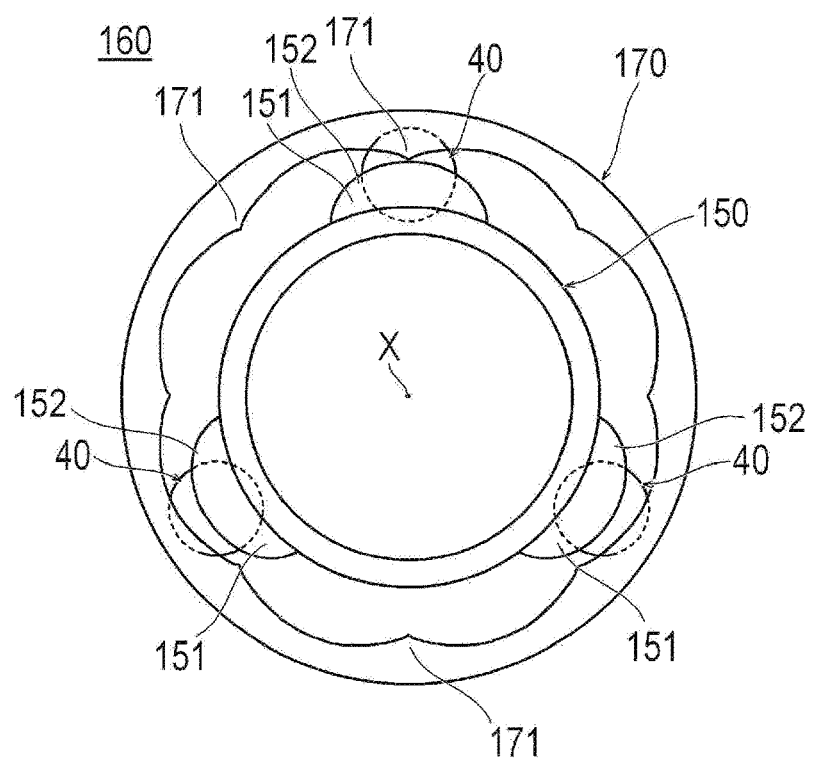
FIG. 12

BEARING AND MEDICAL DEVICE

CROSS-REFERENCES TO RELATED APPLICATIONS

This application is a continuation of International Application No. PCT/JP2018/031816 filed on Aug. 28, 2018, which claims priority to Japanese Application No. 2017-170142 filed on Sep. 5, 2017, the entire content of both of which is incorporated herein by reference.

FIELD OF THE INVENTION

The present invention generally relates to a bearing and a medical device.

BACKGROUND DISCUSSION

In the related art, a rolling bearing includes a rolling element that rolls with respect to an inner ring and an outer ring between the inner ring and the outer ring. An example is disclosed in Japanese Patent Application Publication No. 9-303407 In the rolling bearing, a distance between the rolling elements is maintained by a retainer in order to realize smooth rotation of the rolling elements.

SUMMARY

The retainer fills the gap between the rolling elements. Therefore, it is difficult to actively use the gap between the inner ring and the outer ring of the rolling bearing as a flow path for a fluid such as a liquid or a gas or an object.

Disclosed here is a bearing and a medical device capable of securing a gap between an inner ring and an outer ring and using the gap as a flow path for a fluid or an object.

A bearing disclosed here includes a plurality of rolling elements between an inner ring and an outer ring, in which a raceway surface on which the rolling elements roll is provided on the inner ring or the outer ring, and a receiving portion that rotatably accommodates the rolling elements is provided on a side of the inner ring or the outer ring facing the raceway surface.

A medical device disclosed here is a medical device for cutting an object in a biological lumen. The medical device includes a rotatable drive shaft, a cutting portion provided on a distal side of the drive shaft for cutting the object, an outer tube rotatably accommodating the drive shaft, an inner ring fixed to the cutting portion side, and an outer ring fixed to the outer tube side, in which a raceway surface on which the rolling elements roll is provided on the inner ring or the outer ring, and a receiving portion for rotatably accommodating the rolling element is provided on a side of the inner ring or the outer ring facing the raceway surface.

In the bearing configured as described above, since the inner ring or the outer ring is provided with the receiving portion that rotatably accommodates the rolling element, a retainer for holding the rolling element is unnecessary. Therefore, a gap that penetrates in the axial direction of the bearing between the inner ring and the outer ring can be secured widely, and this gap can be used as a flow path for a fluid, an object, or the like.

In the medical device configured as described above, since the inner ring is provided with the receiving portion that rotatably accommodates the rolling element, a retainer for holding the rolling element is unnecessary. Therefore, a gap that penetrates in the axial direction between the inner ring and the outer ring can be widely secured, and the cut object can be discharged using the gap as a flow path. Therefore, the medical device can simultaneously realize the function of reducing the diameter and the function of circulating the object.

In accordance with another aspect, a bearing includes a first ring, a second ring, a plurality of spherical rolling elements positioned between the first ring and the second ring, wherein the first ring includes a plurality of circumferentially spaced-apart projections that project toward the second ring relative to the portions of the first ring adjacent the projections, and each of the projections includes a convex-shaped receiving portion at which is positioned one of the spherical rolling elements. The second ring includes a raceway surface in contact with the rolling elements and on which the rolling elements roll. The first ring and the second ring are relatively rotatable about a rotation axis of the bearing, and one of the first ring and the second ring is an inner ring of the bearing, and the other of the first ring and the second ring is an outer ring of the bearing.

BRIEF DESCRIPTION OF THE DRAWINGS

FIG. 1 is a plan view showing a bearing according to a first embodiment.

FIGS. 2(A) and 2(B) are views showing the bearing. FIG. 2(A) is a cross-sectional view taken along the section line IIA-IIA of FIG. 1, and FIG. 2(B) is a cross-sectional view showing a first modification example of the bearing.

FIG. 3 is a cross-sectional view taken along the section line III-III in FIG. 2(A).

FIGS. 4(A) and 4(B) are cross-sectional views showing a modification example of the bearing according to the first embodiment. FIG. 4(A) shows a second modification example, and FIG. 4(B) shows a third modification example.

FIG. 5 is a plan view showing a fourth modification example of the bearing according to the first embodiment.

FIG. 6 is a cross-sectional view showing a bearing according to a second embodiment.

FIG. 9(A) is a cross-sectional view, and FIG. 9(B) is an enlarged cross-sectional view in a state where no load is applied.

FIG. 10(A) shows a rotating state in which a load is not applied in the axial direction, and FIG. 10(B) shows a rotating state in which a load is applied in the axial direction and rotated.

FIG. 11 is a cross-sectional view showing a bearing according to a fifth embodiment.

FIG. 12 is a plan view showing a bearing according to a sixth embodiment.

DETAILED DESCRIPTION

Figure 7:
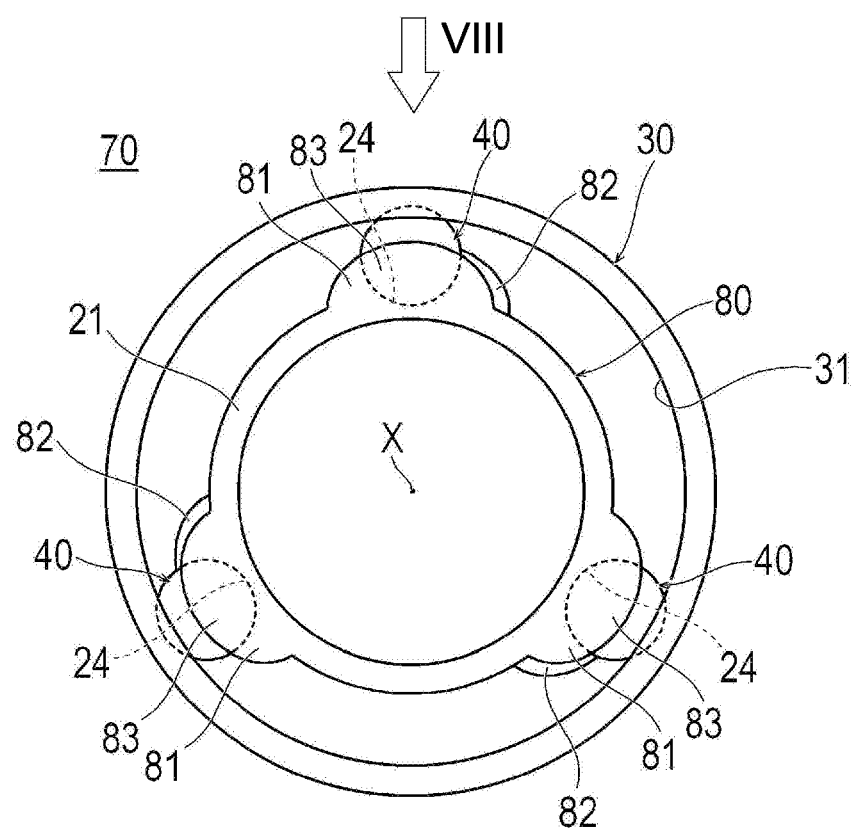
FIG. 7 is a plan view showing a bearing according to a third embodiment.

Set forth below with reference to the accompanying drawings is a detailed description of embodiments of a bearing and a medical device including such bearing representing examples of the inventive bearing and a medical device disclosed here. The dimensions or scales on the drawings may be exaggerated or different from actuality/reality for convenience of description and illustration.

First Embodiment

A bearing 10 according to one embodiment, as shown in FIGS. 1, 2(A), and 3, can secure a gap between an inner ring 20 and an outer ring 30 for circulating a fluid such as a liquid or a gas, an object, or the like. The bearing 10 includes a cylindrical inner ring 20, a cylindrical outer ring 30 disposed so as to surround the inner ring 20, and a plurality of rolling elements 40 disposed between the inner ring 20 and the outer ring 30. The inner ring 20 and the outer ring 30 are relatively rotatable about an axis X of the bearing 10. The axis X is also the axis of the inner ring 20 and the outer ring 30.

Each of the rolling elements 40 is a sphere that can rotate between the inner ring 20 and the outer ring 30. The rolling elements 40 need not be spherical as long as they are rotatable, and may be, for example, cylindrical members. The number of the rolling elements 40 is three in the illustrated embodiment, but is not particularly limited as long as it is two or more. If the number of the rolling elements 40 is three or more, the positions of the inner ring 20 and the outer ring 30, which rotate relatively, can be favorably maintained. The number of the rolling elements 40 is preferably not too large so as to secure a gap between the inner ring 20 and the outer ring 30, and is, for example, six or less.

The inner peripheral surface of the outer ring 30 is provided with a raceway surface 31 on which the rolling elements 40 roll in a contact state (i.e., the rolling elements 40 contact the raceway surface 31). The raceway surface 31 has a groove portion or groove 32 extending in the circumferential direction. The groove portion 32 includes two outer ring wall portions 37 (second wall portions) on both sides in the axial direction. The radius of curvature r1 of the groove portion 32 in the cross section where the axis X of the outer ring 30 is located is slightly larger than the radius R of the rolling elements 40, for example, about 2% to 30% larger. Therefore, the rolling elements 40 can smoothly roll in the groove portion 32. By forming the groove portion 32 in this way, the rolling elements 40 can be prevented from falling off the raceway surface 31, and the rotation of the rolling elements 40 is stabilized. The rolling elements 40 move in the circumferential direction relative to the outer ring 30 by rolling on the raceway surface 31. The rolling elements 40 can slide instead of roll on the raceway surface 31. That is, the rolling elements 40 can also move in the circumferential direction with respect to the outer ring 30 by sliding on the raceway surface 31. Therefore, when it is possible for the rolling elements to roll, it is possible for them to slide according to the conditions. Therefore, even if the rotation of the rolling elements 40 with respect to the raceway surface 31 is stopped, the rolling elements 40 can move with respect to the outer ring 30 by sliding on the raceway surface 31 without rolling. The outer ring 30 is divided into two outer ring constituent members 34 in the groove portion 32 in the axial direction (the direction along the axis X). The two outer ring constituent members 34 attach on a dividing surface 36. Accordingly, the rolling elements 40 on the inner ring 20 are disposed to be interposed between the two outer ring constituent members 34, so that the rolling elements 40 are disposed inside the groove portion 32 of the outer ring 30. The position where the outer ring 30 is divided into the two outer ring constituent members 34 is not particularly limited as long as the rolling elements 40 can be disposed in the groove portion 32 of the outer ring 30.

The inner ring 20 includes a cylindrical inner ring main body 21 having a constant outer diameter, and a plurality of projection portions (projections) 22 provided on the outer peripheral surface of the inner ring main body 21. The projection portions protrude or project radially outward. In the illustrated embodiment disclosed by way of example, there are three projection portions 22. The inner ring 20 may be a solid member instead of a cylindrical shape (hollow shape). Each projection portion 22 is formed with or includes a convex receiving portion 23 that rotatably accommodates the respective rolling element 40. The three projection portions 22 are disposed at equal intervals in the circumferential direction of the inner ring main body 21. The receiving portion 23 of each projection portion 22 has a concave sliding surface 24 on which the outer peripheral surface of the rolling element 40 slides rotatably. Each projection portion 22 has two inner ring wall portions 29 (first wall portions) on both sides in the axial direction with the two sliding surfaces 24 interposed therebetween. In order for the rolling elements 40 to roll on the inner ring 20, the rolling elements 40 need to be able to move relative to the inner ring 20 in the circumferential direction of the inner ring 20 about the axis X. On the other hand, in the present embodiment, because the rolling elements 40 are accommodated in the receiving portions 23, they cannot move relative to the inner ring 20 in the circumferential direction of the inner ring 20 around the axis X. Therefore, the rolling elements 40 do not roll with respect to the inner ring 20, but rather slide inside the respective receiving portions 23. Therefore, when the rotation of the rolling elements 40 with respect to the inner ring 20 is stopped, the rolling elements 40 cannot slide or roll with respect to the inner ring 20, and instead move together with the inner ring 20. At this time, the rolling elements 40 slide without rolling on the raceway surface 31 of the outer ring 30.

The sliding surfaces 24 have a curved shape corresponding to the outer peripheral surface of the rolling elements 40. The radius of curvature r2 of each sliding surface 24 is slightly larger than the radius R of the rolling elements 40, for example, about 2% to 30% larger. Therefore, the rolling elements 40 can smoothly slide on the respective sliding surface 24. The sliding surfaces 24 may be coated with a low friction material so that the frictional resistance is reduced. Examples of the low friction material include diamond-like carbon (DLC) or fluorine-based resin materials such as polytetrafluoroethylene (PTFE), and tetrafluoroethylene-ethylene copolymer (ETFE). The sliding surfaces 24 surround about half of the area of the outer peripheral surface of the respective rolling element 40. Further, the sliding surface 24 may achieve low friction by surface processing such as performing fine unevenness processing. The area where the sliding surface 24 covers the rolling element 40 is not particularly limited as long as the rolling element 40 can be accommodated in the sliding surface 24 and can rotate.

The friction coefficient of the sliding surface 24 is preferably smaller than the friction coefficient of the raceway surface 31. Accordingly, each rolling element 40 smoothly slides and rotates inside the respective receiving portion 23 where the sliding surface 24 is formed. Because the friction coefficient of the raceway surface 31 is larger than the friction coefficient of the sliding surface 24, the rolling elements 40 can roll on the raceway surface 31 without slipping.

In a cross section passing through the center of the rolling element 40 and orthogonal to the axis X of the inner ring 20, as shown in FIG. 3, in the annular range (area=$\pi(R_1^2-R_2^2)$) between the radius $R_1$ of the inner peripheral surface of the outer ring 30 and the radius R2 of the outer peripheral surface of the inner ring main body 21, the ratio occupied by the projection portions 22 and the rolling elements 40 is 75% or less, more preferably 50% or less, and further preferably 35% or less. As the amount of space occupied by the projection portions 22 and the rolling elements 40 becomes smaller with respect to the area (area=$\pi(R_1^2-R_2^2)$) between the inner ring main body 21 and the outer ring 30, a wide gap penetrating in the axial direction between the inner ring 20 and the outer ring 30 is secured or ensured. Accordingly, a fluid and an object can satisfactorily flow through the gap between the inner ring 20 and the outer ring 30.

The outer ring wall portion 37 has a height $H_2$ from the bottom of the groove portion 32 (the outermost position in the radial direction). The inner ring wall portion 29 has a height $H_1$ from the bottom of the sliding surface 24 (the innermost position in the radial direction). The outer ring wall portion 37 is located radially outward of the inner ring wall portion 29 at a predetermined interval. The height $H_2$ of the outer ring wall portion 37 is smaller than the height $H_1$ of the inner ring wall portion 29. Therefore, a gap penetrating in the axial direction between the outer ring 30 and the inner ring 20 is provided at a position away from the axis X. Since the width of the gap depends on the circumference around the axis X, the gap increases as the distance from the axis X increases. Therefore, since the height $H_2$ of the outer ring wall portion 37 is smaller than the height $H_1$ of the inner ring wall portion 29, it is easy to secure a wide gap penetrating in the axial direction between the outer ring 30 and the inner ring 40. Accordingly, a fluid or an object can satisfactorily flow in the gap between the outer ring 30 and the inner ring 40.

According to a first modification example shown in FIG. 2(B), the inner ring 20 may be divided into two inner ring constituent members 26 in the axial direction. The two inner ring constituent members 26 attach on a dividing surface 28 passing through the receiving portions 23. Accordingly, the rolling elements 40 can be disposed in the respective receiving portions 23 of the inner ring 20 by overlapping the two inner ring constituent members 26 so that the rolling elements 40 can be interposed therebetween. In this case, the area where each receiving portion 23 surrounds the respective rolling element 40 can be larger than the area when the inner ring 20 is not divided. For example, when the inner ring 20 is not divided, the opening portion of each receiving portion 23 of the inner ring 20 needs to be large enough to allow the respective rolling element 40 to be inserted. On the other hand, when the inner ring 20 is divided, the opening portion of each receiving portion 23 of the inner ring 20 may have such a size that the rolling element 40 cannot be inserted. In this case, the respective rolling element 40 can be accommodated in the receiving portion 23 by interposing the rolling element 40 between the two inner ring constituent members 26. Therefore, the inner ring 20 can also cover a range that exceeds half of the outer surface of the rolling element 40. Since the inner ring 20 covers a wide area of the outer surface of the rolling elements 40, entry of foreign substances (foreign matter) into the gap between the receiving portion 23 and the rolling element 40 can be suppressed.

As the material of the outer ring 30, the inner ring 20, and the rolling element 40, for example, materials used for general bearings such as stainless steel, ceramics, and resin can be used. The outer ring 30, the inner ring 20, and the rolling elements 40 may be made of different constituent materials.

Next, the operation of the bearing 10 according to the first embodiment will be described.

When the inner ring 20 and the outer ring 30 of the bearing 10 shown in FIGS. 1 to 3 rotate relatively, the rolling elements 40 roll on the raceway surface 31 of the outer ring 30. The rolling elements 40 may slide on the raceway surface 31 of the outer ring 30. Further, the rolling elements 40 slide on the sliding surface 24 and rotate while being accommodated in the respective receiving portions 23 of the inner ring 20. At this time, since there is no retainer between the inner ring 20 and the outer ring 30, a large gap penetrating in the axial direction of the bearing 10 is secured. Therefore, a fluid or an object can satisfactorily flow through the gap between the inner ring 20 and the outer ring 30. Further, the flow of a fluid or an object through the gap between the inner ring 20 and the outer ring 30 can suppress heat generation of the bearing 10.

As described above, the bearing 10 according to the first embodiment is a bearing 10 having a plurality of rolling elements 40 between an inner ring 20 and an outer ring 30, in which a raceway surface 31 on which the rolling elements 40 roll is provided on the outer ring 30, and a receiving portion 23 for rotatably accommodating the rolling elements 40 is provided at a position facing the raceway surface 31 of the outer ring 20.

In the bearing 10 configured as described above, since the inner ring 20 is provided with the receiving portions 23 that rotatably accommodate the respective rolling elements 40, a retainer for holding the rolling elements 40 is unnecessary. Therefore, a relatively wide gap that penetrates in the axial direction of the bearing 10 between the inner ring 20 and the outer ring 30 can be achieved, and this gap can be used as a flow path for a fluid, an object, or the like.

Further, the receiving portions 23 are each formed in a convex shape in which the inner ring 20 provided with the receiving portion 23 protrudes toward the raceway surface 31. Therefore, the spaces between the adjacent receiving portions 23 on the outer peripheral surface of the inner ring 20 are formed in a concave shape or possess a concave shape. Therefore, axially extending gaps exist between the concave portion (the portion where the receiving portion 23 is not provided) on the outer peripheral surface of the inner ring 20 and the raceway surface 31. Accordingly, this makes it possible to secure relatively wide gaps between the convex receiving portions 23, and this facilitates the flow of the fluid or the object. Further, the entry of foreign substances (foreign matter) between the receiving portion 23 and the rolling element 40 can be suppressed by the convex receiving portion 23.

Further, the friction coefficient of the sliding surface 24 of the receiving portion 23 in contact with the rolling elements 40 is smaller than the friction coefficient of the raceway surface 31. Accordingly, the rolling elements 40 can roll on the raceway surface 31 while sliding and rotating on the sliding surface 24 in a state of being accommodated in the respective receiving portion 23.

Further, the material of the sliding surface 24 of the receiving portion 23 in contact with the rolling elements 40 may be different from the material of the raceway surface 31.

Accordingly, this makes it easy to make the friction coefficient of the sliding surface 24 smaller than the friction coefficient of the raceway surface 31.

Further, the surface microstructure of the sliding surface 24 of the receiving portion 23 in contact with the rolling elements 40 may be different from the surface microstructure of the raceway surface 31. Accordingly, this makes it easy to make the friction coefficient of the sliding surface 24 smaller than the friction coefficient of the raceway surface 31.

The shape of the groove portion 32 is not particularly limited as long as the rolling elements 40 can be rotatably accommodated. For example, in a second modification example shown in FIG. 4(A), the groove portion 32 of the outer ring 30 may include a flat (linear) first bottom surface 33 in a cross section where the axis X of the outer ring 30 is located.

Further, as in the third modification example shown in FIG. 4(B), the concave sliding surface 24 of the receiving portion 23 may include a flat (linear) second bottom surface 25 in a cross section where the axis X of the inner ring 20 is located.

Further, as in a fourth modification example shown in FIG. 5, a receiving portion 35 for rotatably accommodating the rolling element 40 may be provided on the outer ring 30, and a raceway surface 27 may be provided on the inner ring 20. Further, the raceway surface of the outer ring 30 (or the inner ring 20) may not have a groove.

Second Embodiment

As shown in FIG. 6, a bearing 50 according to a second embodiment is different from the first embodiment in that a flow hole 62 for supplying a fluid to a receiving portion 61 of an inner ring 60 is formed. In the description below, features that have the same or similar functions to those described above are identified by the same reference numerals and a detailed description of such features is not repeated.

In the inner ring 60 of the bearing 50, the flow hole 62 for supplying a fluid to the sliding surface 24 is formed in each receiving portion 61. Each flow hole 62 (through hole) penetrates from the inner peripheral surface of the inner ring 60 to the sliding surface 24.

Next, the operation of the bearing 50 according to the second embodiment will be described.

The bearing 50 according to the second embodiment can supply a fluid such as water, oil, air, or gas from the inner peripheral surface side of the inner ring 60 to the sliding surface 24 through the flow hole 62. When the fluid is supplied to the sliding surface 24, the fluid reduces the friction between the sliding surface 24 and the rolling elements 40. Accordingly, the friction coefficient of the sliding surface 24 decreases, and the rolling element 40 can be satisfactorily rotated. Further, when the fluid is supplied to the sliding surface 24, contamination of the sliding surface 24 with foreign substances can be suppressed, and good rotation of the rolling element 40 can be maintained. When a fluid is disposed on the inner peripheral surface side of the inner ring 60, the inner ring 60 rotates, so that the fluid can be automatically supplied from the flow hole 62 to the sliding surface 24 by centrifugal force. Note that, the flow hole 62 may be formed by a hole made of a porous material that forms the sliding surface 24. That is, the portion of the inner ring forming the sliding surface 24 may be made of porous material that naturally provides the flow hole(s) for fluid to flow to the sliding surface. Further, by pressurizing the fluid, it is also possible to positively supply the fluid through the flow hole 62.

Note that, when the outer ring 30 is provided with a receiving portion that rotatably accommodates the rolling element 40, the flow hole is provided in the outer ring 30.

Third Embodiment

Figure 8:
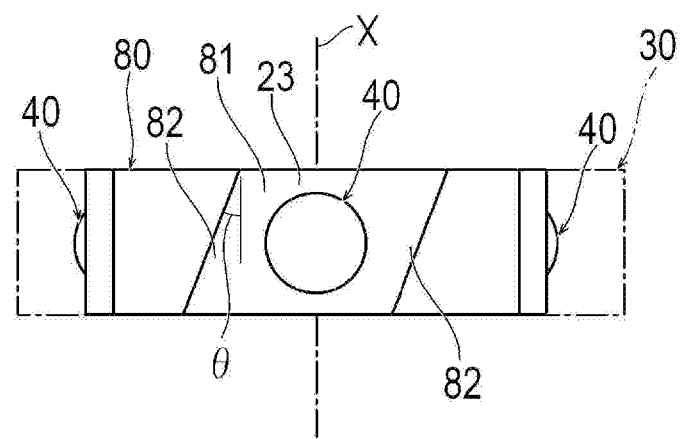
FIG. 8 is a perspective view of an outer ring viewed through arrow VIII in FIG. 7.

As shown in FIG. 7 and FIG. 8, which is a perspective view of the outer ring 30 as viewed through arrow C in FIG. 7, a bearing 70 according to a third embodiment is different from the first embodiment only in the shape of a projection portion 81 of an inner ring 80. In the description below, features having the same or similar functions to those in embodiments described above are identified by the same reference numerals and a detailed description of such features is not repeated.

Each projection portion 81 provided on the inner ring 80 of the bearing 70 has a convex receiving portion 83. The convex receiving portion 83 has a slope 82 inclined on the side surface of the inner ring 80 in the rotation direction with respect to the axis X of the inner ring 80. The directions in which the slopes 82 of the three receiving portions 83 are inclined are the same in the rotation direction of the inner ring 80. The inclination angle $\theta$ of the slope 82 with respect to the axis X of the inner ring 80 is more than 0 degrees and less than 90 degrees, preferably 20 degrees or more and 70 degrees or less, more preferably 30 degrees or more and 60 degrees or less.

Next, the operation of the bearing 70 according to the third embodiment will be described.

When the inner ring 80 rotates, the receiving portion 83 having the slope 82 inclined with respect to the axis X of the inner ring 80 plays a role of a screw blade, and a fluid or an object existing in the gap between the inner ring 80 and the outer ring 30 moves along the axial direction of the inner ring 80. Therefore, the rotation of the inner ring 80 can be used to generate a flow in the gap between the inner ring 80 and the outer ring 30.

A convex receiving portion serving as a screw blade may be provided on the outer ring 30. In this case, the rotation of the outer ring 30 can be used to generate a flow in the gap between the inner ring 80 and the outer ring 30.

Fourth Embodiment

Figure 9A:
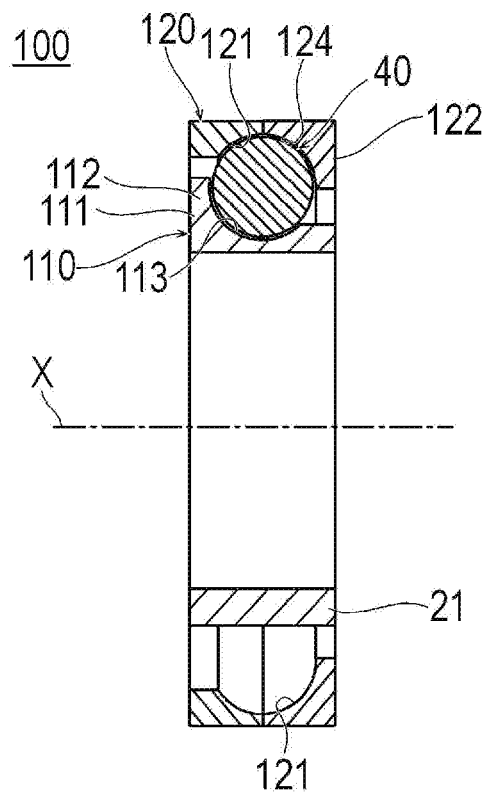
FIGS. 9(A) and 9(B) are views showing a bearing according to a fourth embodiment.
Figure 9B:
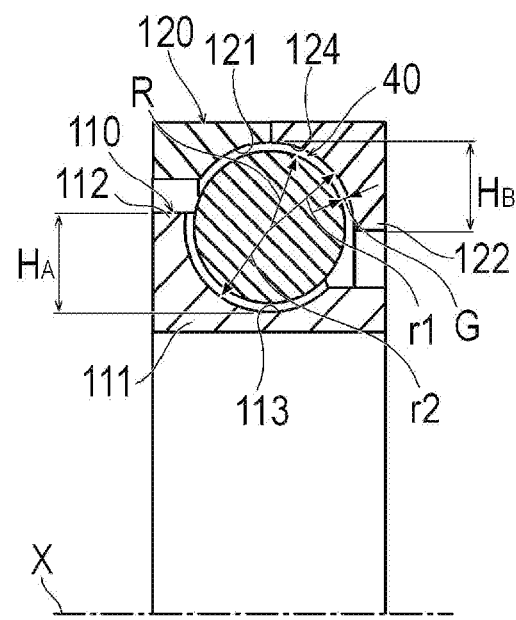

As shown in FIG. 9(A) and the enlarged FIG. 9(B), a bearing 100 according to a fourth embodiment is different from the first embodiment in the structure of a receiving portion 111 of an inner ring 110 and a groove portion 121 of an outer ring 120. In the description below, features that have the same or similar function to those in embodiments described above are identified by the same reference numerals and a detailed description of such features is not repeated.

The receiving portion 111 of the inner ring 110 of the bearing 100 according to the fourth embodiment includes an inner ring wall portion 112 (first wall portion) that is higher radially outward on one side in the axial direction in a cross section where the axis X of the inner ring 110 is located. That is, as shown in FIG. 9(B), the inner ring wall portion 112 (first wall portion) is radially farther away from the axis X on one axial side compared to the other axial side (i.e., the perpendicular distance between the axis X and the free end of the inner ring wall portion 112 is greater than the perpendicular distance between the axis X and the free end of the inner ring wall portion on the other axial side of the bearing). When the height from the bottom of a sliding surface 113 of the inner ring 110 (the innermost position in the radial direction) to the outer peripheral surface of the inner ring wall portion 112 is defined as $H_A$, and the radius of the rolling elements 40 is defined as R, it is preferable that the following formula (1) is satisfied, and it is more preferable that the following formula (2) is satisfied. Accordingly, the inner ring wall portion 112 can limit the movement of the rolling elements 40 in the axial direction. Therefore, the bearing 100 can favorably receive not only a load in the radial direction but also a load in the axial direction. The formula (2) may not be satisfied in some cases.

$$H_A > 0 \quad \text{Formula (1)}$$

$$H_A \geq R \quad \text{Formula (2)}$$

Further, the groove portion 121 of the outer ring 120 has an outer ring wall portion 122 (second wall portion) that is higher radially inward on one side in the axial direction in a cross section where the axis X of the outer ring 120 is located. That is, as shown in FIG. 9(B), the outer ring wall portion 122 (second wall portion) on one axial side of the bearing is radially closer toward the axis X compared to the outer ring wall on the other axial side (i.e., the perpendicular distance between the axis X and the free end of the outer ring wall portion 122 is greater than the perpendicular distance between the axis X and the free end of the outer ring wall portion on the other axial side of the bearing). The outer ring wall portion 122 is disposed on the opposite side of the inner ring wall portion 112 with the rolling elements 40 interposed therebetween. When the height from the bottom of a raceway surface 124 of the outer ring 120 (the outermost position in the radial direction) to the inner peripheral surface of the outer ring wall portion 122 is defined as $H_B$, it is preferable that the following formula (3) is satisfied, and it is more preferable that the following formula (4) is satisfied. Accordingly, the outer ring wall portion 122 can limit the movement of the rolling elements 40 in the axial direction. Therefore, the bearing 100 can receive a load in the axial direction. The formula (4) may not be satisfied in some cases.

$$H_B > 0 \quad \text{Formula (3)}$$

$$H_B \geq R \quad \text{Formula (4)}$$

In a state before the bearing 100 according to the fourth embodiment rotates, each rolling element 40 is theoretically located with a gap G with respect to the sliding surface 113 and the raceway surface 124. When the radius of the rolling element 40 is defined as R, the following formula (5) is preferably satisfied, and more preferably, the following formula (6) is satisfied. Accordingly, the gap G does not become too large with respect to the radius R of the rolling element 40, and the rotation is stabilized and the loss is reduced. The gap G may change depending on the position of the sliding surface 113.

$$0 < G \leq 2 \times R \times 0.1 \quad \text{Formula (5)}$$

$$0 < G \leq 2 \times R \times 0.05 \quad \text{Formula (6)}$$

When the radius of curvature of the raceway surface 124 in the cross section where the axis X is located is defined as r1, the following formula (7) is preferably satisfied, and more preferably the following formula (8) is satisfied. Accordingly, the radius of curvature r1 of the raceway surface 124 does not become too large with respect to the radius R of the rolling element 40 that comes into contact with the raceway surface 124, and the rolling elements 40 easily roll on the raceway surface 124.

$$r1 \leq 1.5 \times R \quad \text{Formula (7)}$$

$$r1 \leq 1.25 \times R \quad \text{Formula (8)}$$

When the radius of curvature of the sliding surface 113 in the cross section where the axis X is located is defined as r2, the following formula (9) is preferably satisfied, and more preferably formula (10) is satisfied. Accordingly, the radius of curvature r2 of the sliding surface 113 does not become too large with respect to the radius R of the rolling element 40 that comes into contact with the sliding surface 113, and the rolling element 40 slides easily on the raceway surface 124.

$$r2 \leq 1.5 \times R \quad \text{Formula (9)}$$

$$r2 \leq 1.25 \times R \quad \text{Formula (10)}$$

The radius of curvature r1 of the raceway surface 124 and the radius of curvature r2 of the sliding surface 113 may be the same or one of them may be larger, but it is preferable that the following formula (11) is satisfied. The radius of curvature r1 of the raceway surface 124 is closer to the radius R of the rolling element 40 than the radius of curvature r2 of the sliding surface 113. Therefore, the raceway surface 124 comes into contact with the rolling element 40 more strongly than the sliding surface 113. Therefore, the rolling element 40 is suppressed from sliding on the raceway surface 124, and easily rolls on the raceway surface 124.

$$r1 < r2 \quad \text{Formula (11)}$$

Next, the operation of the bearing 100 according to the fourth embodiment will be described.

Figure 10A:
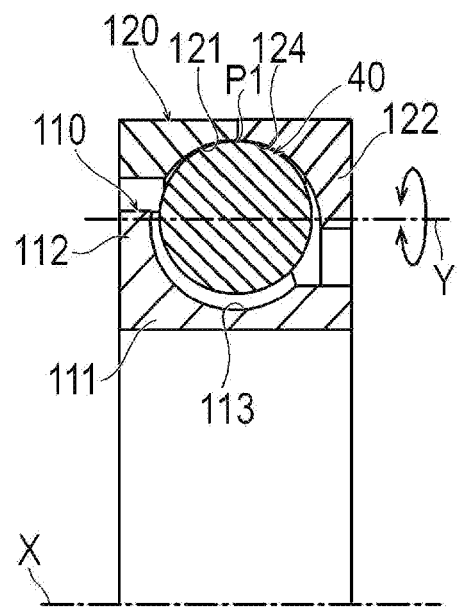
FIGS. 10(A) and 10(B) are sectional views showing the bearing according to the fourth embodiment.

When the bearing 100 according to the fourth embodiment rotates, in a state where no load is applied or in a state where a load is applied in the radial direction, as shown in FIG. 10(A), the rolling elements 40 move radially outward due to the centrifugal force and the force received from the sliding surface 113. Accordingly, the rolling elements 40 come into contact with the raceway surface 124 at a radially outward position P1. Since the rolling element 40 receives a force from the raceway surface 124 at the position P1, the rotation axis Y of the rolling element 40 is substantially parallel to the axis X of the bearing 100. The rolling elements 40 can roll on the raceway surface 124 of the outer ring 120 while sliding on the sliding surface 113 of the receiving portion 111.

Figure 10B:
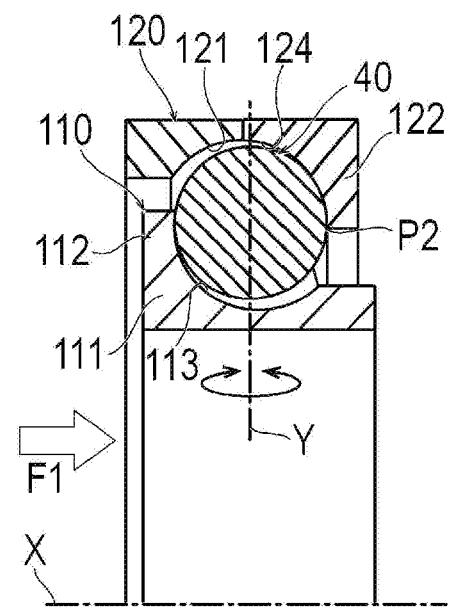

When a load F1 is applied in the axial direction so as to interpose the rolling element 40 between the inner ring wall portion 112 and the outer ring wall portion 122, as shown in FIG. 10(B), the rolling elements 40 come into contact with the raceway surface 124 at a position P2 on the axial direction side. Since the rolling element 40 receives a force from the raceway surface 124 at the position P2, the rotation axis Y of the rolling element 40 is substantially orthogonal to the axis X of the bearing 100. The rolling elements 40 can roll on the raceway surface 124 of the outer ring wall portion 122 while sliding on the sliding surface 113 of the inner ring wall portion 112.

As shown in the formula (2), since the height $H_A$ of the inner ring wall portion 112 is higher than the radius R of the rolling element 40, the inner ring wall portion 112 is can favorably receive the axial force from the rolling elements 40. Further, as shown in the formula (4), since the height $H_B$ of the outer ring wall portion 122 is higher than the radius R of the rolling element 40, the outer ring wall portion 122 can favorably receive the axial force from the rolling elements 40. Therefore, the bearing 100 is relatively easily subjected to the load F1 in the axial direction, and the load resistance in the axial direction is improved. The rotation axis Y of the rolling elements 40 is not limited to be parallel or orthogonal to the axial direction, and may be inclined at less than 90 degrees with respect to the axial direction. For example, when the height $H_A$ of the inner ring wall portion 112 is lower than the radius R of the rolling element 40 (when the formula (2) is not satisfied), or when the height $H_B$ of the outer ring wall portion 122 is lower than the radius R of the rolling element 40 (when the formula (4) is not satisfied), the rotation axis Y of the rolling elements 40 is unlikely to be orthogonal to the axial direction. Therefore, when the bearing 100 receives the load F1 in the axial direction, the rotation axis Y of the rolling elements 40 tends to be inclined at less than 90 degrees with respect to the axial direction.

The position P2 at which the rolling elements 40 come into contact with the outer ring 120 when the load F1 is applied in the axial direction is closer to the rotation center of the bearing 100 than the position P1 (see FIG. 10(A)) at which the rolling elements 40 comes into contact with the outer ring 120 when the load F1 is not applied. In the state where the load F1 is applied on the bearing 100 in the axial direction (state where contact is made at the position P2), the radius of gyration at the position where the rolling elements 40 roll with respect to the raceway surface 124 is smaller and the rolling distance is shorter than in the state where the load F1 is not applied (state where contact is made at position P1). Therefore, the amount of heat generated by friction can be reduced. Therefore, the bearing 100 has a small rotation resistance and can rotate efficiently with a low driving force.

Further, the receiving portion 111 has an inner ring wall portion 112 (first wall portion) located on the axial direction side of the bearing 100 with respect to the rolling elements 40, the raceway surface 124 has an outer ring wall portion 122 (second wall portion) located on the axial direction side of the bearing 100 with respect to the rolling elements 40, and the rolling elements 40 are interposed and supported between the inner ring wall portion 112 and the outer ring wall portion 122 in the axial direction. Therefore, the bearing 100 can change the direction of the rotation axis Y of the rolling elements 40 in accordance with the direction of the applied load. Therefore, the bearing 100 can receive not only the load in the radial direction but also the load F1 in the axial direction.

Fifth Embodiment

A bearing 130 according to a fifth embodiment differs from the fourth embodiment in that the rolling elements 40 are provided in two rows in the axial direction as shown in FIG. 11. Features in this embodiment having the same or similar functions to those described above are identified by the same reference numerals and a detailed description of such features is not repeated.

The inner peripheral surface of an outer ring 140 is provided with a raceway surface 141 on which the rolling elements 40 roll in a contact state. The raceway surface 141 is formed with a groove portion 142 extending in the circumferential direction. The groove portion 142 can accommodate first rolling elements 41 and second rolling elements 42 disposed in the axial direction of the outer ring 140. The groove portion 142 includes a first outer ring wall portion 143 (second wall portion) and a second outer ring wall portion 144 (second wall portion) on opposite sides in the axial direction. The first outer ring wall portion 143 comes into contact with the first rolling elements 41. The second outer ring wall portion 144 comes into contact with the second rolling elements 42. By forming the groove portion 142, the first rolling elements 41 and the second rolling elements 42 can be prevented from falling off from the raceway surface 141, and the rotation of the first rolling elements 41 and the second rolling elements 42 is stabilized. The outer ring 140 is divided into two outer ring constituent members 145 in the axial direction at the dividing surface 146 of the groove portion 142. Accordingly, by overlapping the two outer ring constituent members 145 on the dividing surface 146 so as to interpose the first rolling elements 41 and the second rolling elements 42 disposed on an inner ring 150, the first rolling elements 41 and the second rolling elements 42 can be disposed in the groove portion 142 of the outer ring 140. It is preferable that the two outer ring constituent members 145 have a configuration in which the rolling elements 40 are interposed between the first outer ring wall portion 143 and the second outer ring wall portion 144 (front combination) from the viewpoint of assembling accuracy and the allowable inclination angle of the load.

The inner ring 150 includes three projection portions 151 protruding radially outward on the outer peripheral surface of the inner ring. The three projection portions 151 are disposed at equal intervals in the circumferential direction of the inner ring 150. Each projection portion 151 includes a convex receiving portion 152 that rotatably accommodates the first rolling element 41 and the second rolling element 42. The two receiving portions 152 of each projection portion 151 are disposed in the axial direction of the inner ring 150. Each receiving portion 152 has a concave sliding surface 154 on which the outer peripheral surfaces of the first rolling element 41 and the second rolling element 42 slide.

Each projection portion 151 includes an inner ring wall portion 153 (first wall portion) that is higher radially outward between the first rolling element 41 and the second rolling element 42 arranged in the axial direction. The first rolling element 41 is rotatably disposed between the first outer ring wall portion 143 and the inner ring wall portion 153. Further, the second rolling element 42 is disposed between the second outer ring wall portion 144 and the inner ring wall portion 153.

Next, the operation of the bearing 130 according to the fifth embodiment will be described.

When the load F2 is applied in the axial direction so as to interpose the first rolling elements 41 between the inner ring wall portion 153 and the first outer ring wall portion 143, similarly to the theory described in the fourth embodiment, the rotation axis Y of the first rolling elements 41 approaches a direction orthogonal to the axis X of the bearing 130. Accordingly, the rolling elements 40 can roll on the raceway surface 141 of the first outer ring wall portion 143 while sliding on the sliding surface 154 of the inner ring wall portion 153.

When the load F3 in the direction opposite to the load F2 is applied in the axial direction so as to interpose the second rolling elements 42 between the inner ring wall portion 153 and the second outer ring wall portion 144, similarly to the theory described in the fourth embodiment, the rotation axis Y of the second rolling elements 42 approaches a direction orthogonal to the axis X of the bearing 130. Accordingly, the second rolling elements 42 can roll on the raceway surface 141 of the second outer ring wall portion 144 while sliding on the sliding surface 154 of the inner ring wall portion 153.

In the bearing 130, in a state in which no load is applied or a state in which a load is applied in the radial direction, the rotation axis Y of the first rolling elements 41 and the second rolling elements 42 is substantially parallel to the axis X of the bearing 130. Therefore, the bearing 130 can receive the load in the radial direction and the loads F2 and F3 in the axial direction.

Sixth Embodiment

A bearing 160 according to a sixth embodiment differs from the fifth embodiment only in the shape of an outer ring 170, as shown in FIG. 12. In the description below, features that have the same or similar function to those described above are identified by the same reference numerals and a detailed description of such features is not repeated.

The inner peripheral surface of the outer ring 170 of the bearing 160 is provided with at least one cutting projection portion 171 protruding radially inward at both edge portions in the axial direction. A plurality (eight in the present embodiment) of cutting projection portions 171 are arranged in the circumferential direction on each edge portion of the outer ring 170 in the axial direction. The number of cutting projection portions 171 is not particularly limited. The cutting projection portion 171 can be located radially outward the projection portion 151 provided on the inner ring 150. The cutting projection portion 171 is formed at a height that does not hinder the rotation of the projection portion 151 provided on the inner ring 150. Note that, the cutting projection portion 171 may be provided only on one edge portion of the outer ring 170 in the axial direction.

Next, the operation of the bearing 160 according to the sixth embodiment will be described.

When the inner ring 150 and the outer ring 170 rotate relatively, the object existing in the gap between the inner ring 150 and the outer ring 170 is cut or broken by the relatively rotating convex receiving portion 152 and the cutting projection portion 171. That is, when the inner ring 150 rotates, the convex receiving portions 152 and the cutting projection portions 171 play the role of a cutting blade. Therefore, it becomes easy to transport an object from the gap between the inner ring 150 and the outer ring 170. In the case where the projection portions are disposed on the outer ring 170, the cutting projection portions are provided on the outer peripheral surface of the inner ring 150.

Seventh Embodiment

Figure 13:
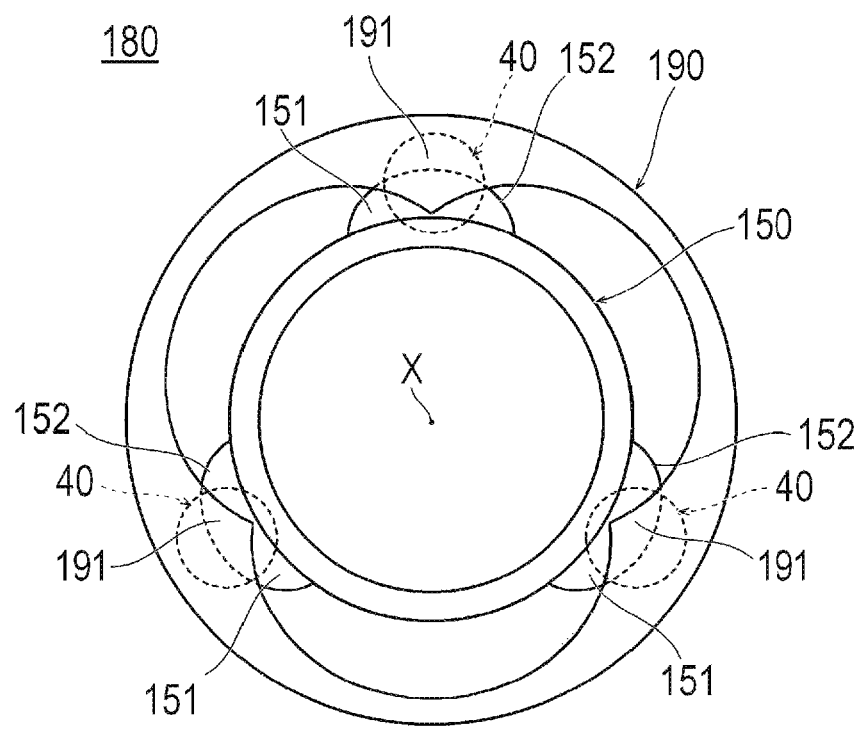
FIG. 13 is a plan view showing a bearing according to a seventh embodiment.

A bearing 180 according to a seventh embodiment differs from the sixth embodiment only in the shape of an outer ring 190, as shown in FIG. 13. Features in this embodiment having the same or similar functions to those described above are identified by the same reference numerals and a detailed description of such features is not repeated.

The inner peripheral surface of the outer ring 190 of the bearing 180 is provided with at least one cutting projection portion 191 protruding radially inward on both edge portions in the axial direction. A plurality (three in the present embodiment) of the cutting projection portions 191 are arranged in the circumferential direction on at least one edge portion of the outer ring 190 in the axial direction. The number of cutting projection portions 191 is not particularly limited. The cutting projection portions 191 are shifted in the axial direction with respect to the projection portion 151 provided on the inner ring 150. It is preferable that the cutting projection portion 191 be disposed with a small interval (clearance) in the axial direction with respect to the projection portion 151. The inner diameter of the outer ring 190 at the top (the innermost position in the radial direction) of the cutting projection portion 191 is smaller than the outer diameter of the inner ring 150 at the top (the outermost position in the radial direction) of the projection portion 151.

Next, the operation of the bearing 180 according to the seventh embodiment will be described.

When the inner ring 150 and the outer ring 190 rotate relatively, the object existing in the gap between the inner ring 150 and the outer ring 190 is cut or broken by the relatively rotating projection portion 151 and cutting projection portion 191. At this time, the inner diameter of the outer ring 190 at the top of the cutting projection portion 191 is smaller than the outer diameter of the inner ring 150 at the top of the projection portion 151. Therefore, when the inner ring 150 rotates, the object interposed between the projection portion 151 and the cutting projection portion 191 is effectively cut by receiving a shear force from the projection portion 151 and the cutting projection portion 191. Therefore, it becomes easy to transport the object from the gap between the inner ring 150 and the outer ring 190.

<Application Example of Bearing to Medical Device>

Figure 14:
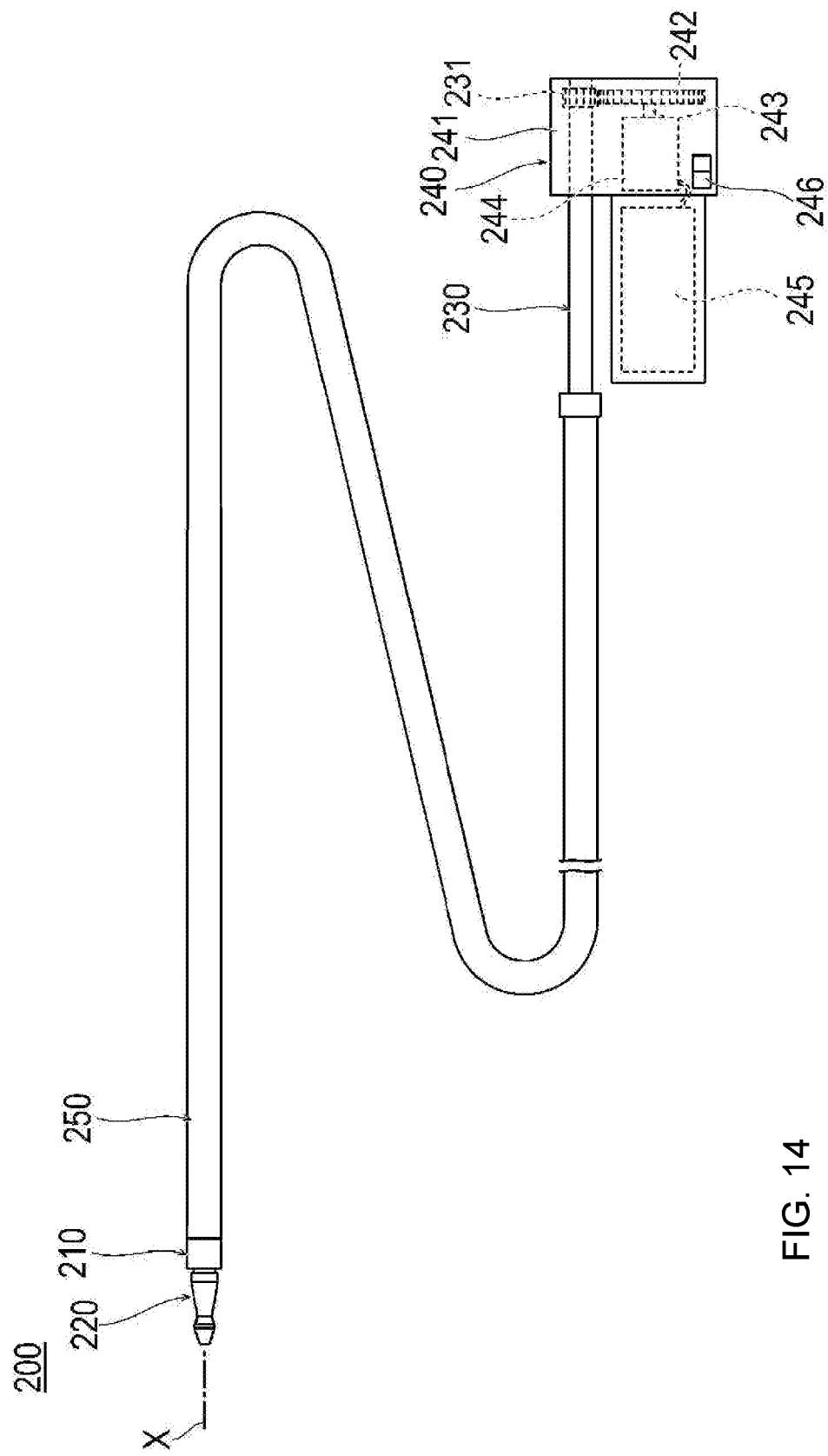
FIG. 14 is a plan view showing a medical device to which a bearing is applied.
Figure 15:
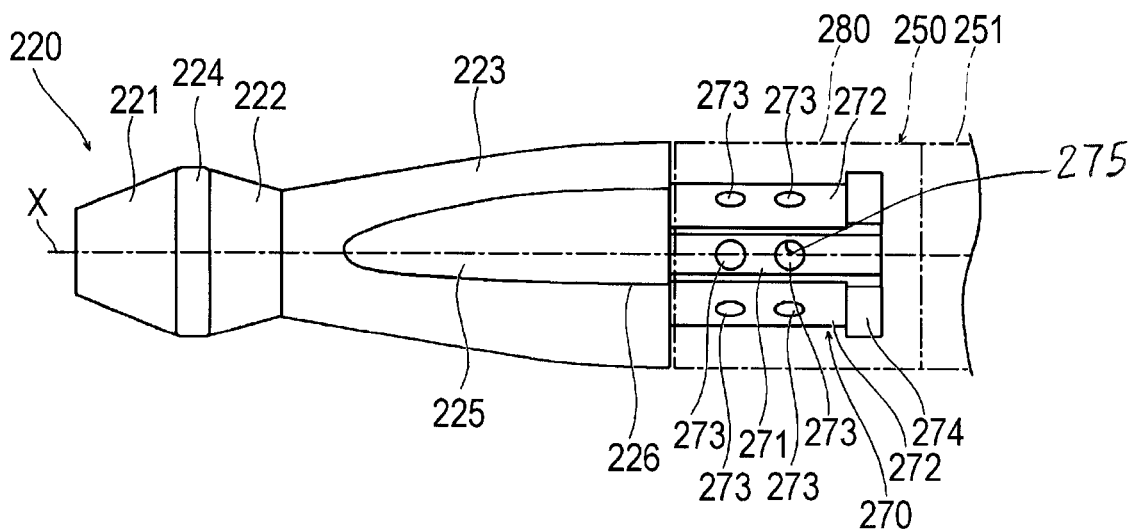
FIG. 15 is a plan view showing a structure of the medical device.
Figure 16:
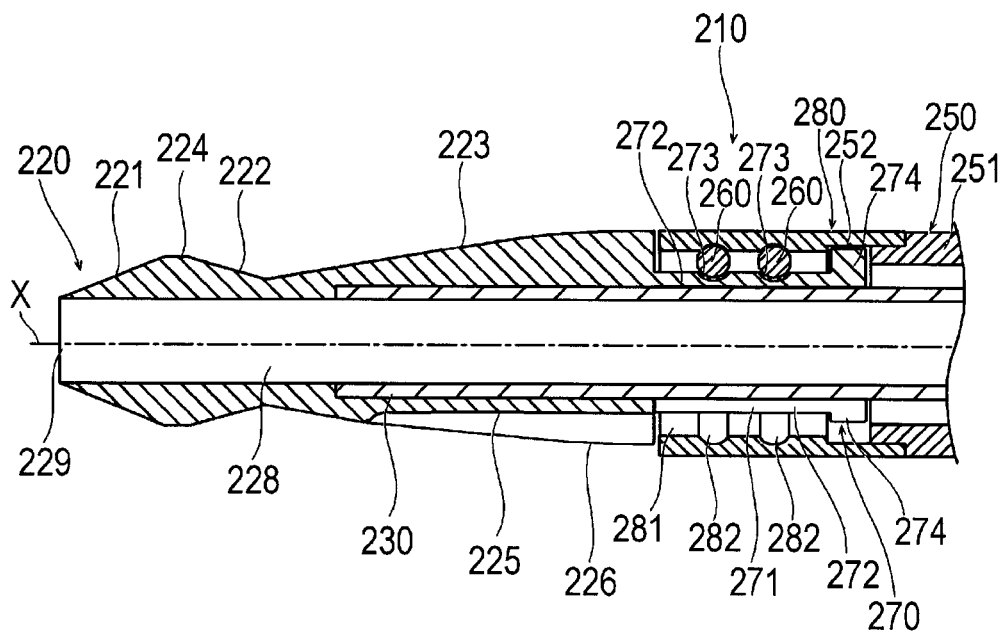
FIG. 16 is a cross-sectional view showing a distal portion of the medical device.

FIGS. 14-16 illustrate a medical device 200 to which a bearing 210 is applied. This medical device, disclosed as an example of a medical device to which the bearing disclosed here may be applied, is used for a treatment for cutting an object in a biological lumen, for example, a therapy (treatment) for cutting a stenosed site formed by plaque or thrombus in a blood vessel. In the description which follows, the side or end of the device to be inserted into a blood vessel is referred to as the "distal side" or "distal end", and the hand-side for operation is referred to as the "proximal side" or "proximal end".

The medical device 200 includes a rotatable structure 220, a drive shaft 230 that rotates the structure 220, an operation unit 240 provided on the hand-side, an outer sheath 250 that can accommodate the structure 220, and a rolling element 260. The bearing 210 is constituted by a part of the structure 220, the rolling element 260, and a part of the outer sheath 250.

The outer sheath 250 is a tubular body that covers the outside of the drive shaft 230, and is rotatable with respect to the drive shaft 230. The outer sheath 250 has a flexible outer tube 251 which is a long tubular body, and an outer ring 280 fixed to a distal portion of the outer tube 251. An engagement concave portion 252, which is a groove extending over 360 degrees, is formed on the inner peripheral surface between the outer ring 280 and the outer tube 251.

The structure 220 includes a cutting portion for cutting a stenosed site, which is an object in a biological lumen, and a non-cutting portion 224 which makes more smooth contact with the biological tissue than the cutting portion and hardly damages the biological tissue. Further, the structure 220 includes an inner ring 270.

The cutting portion includes a first cutting portion 221 located at the most distal side of the structure 220, a second cutting portion 222 located on the proximal side of the first cutting portion 221, and a third cutting portion 223 located on the proximal side of the second cutting portion 222. The non-cutting portion 224 is located between the first cutting portion 221 and the second cutting portion 222. That is, the structure 220 has the first cutting portion 221, the non-cutting portion 224, the second cutting portion 222, and the third cutting portion 223, which are arranged in that order from the distal end to the proximal side. The structure 220 is a rigid body that hardly bends.

The first cutting portion 221 is located at the most distal portion of the structure 220. The first cutting portion 221 has an outer peripheral surface whose outer diameter decreases in a tapered shape toward the distal side. The outer peripheral surface of the first cutting portion 221 is circular in an axially orthogonal cross section. Inside the structure 220, there is formed a guide wire lumen 228 through which the lumen of the drive shaft 230 communicates and into which a guide wire can be inserted. The guide wire lumen 228 opens at a distal opening portion 229 of the structure 220.

The second cutting portion 222 has an outer peripheral surface whose outer diameter decreases in a tapered shape from the non-cutting portion 224 to the third cutting portion 223 toward the proximal side. The outer peripheral surface of the second cutting portion 222 is circular in an axially orthogonal cross section. The third cutting portion 223 has an outer peripheral surface whose outer diameter increases in a tapered shape from the second cutting portion 222 toward the proximal side. The outer peripheral surface of the third cutting portion 223 is circular in an axially orthogonal cross section.

The second cutting portion 222 and the third cutting portion 223 are interlocked such that the outer peripheral surface has a V-shape in a vertical section passing through the axis X. The maximum radius of the outer peripheral surface of the third cutting portion 223 is larger than the maximum radius of the outer peripheral surface of the second cutting portion 222. The first cutting portion 221 and the third cutting portion 223 cut the stenosed site mainly when pushing the medical device 200 in the forward direction (i.e., to the left in FIGS. 15 and 16). The second cutting portion 222 cuts the stenosed site mainly when the medical device 200 is pulled in the rearward direction (i.e., to the right in FIGS. 15 and 16). An abrasive such as, for example, diamond particles is fixed to the outer surfaces of the first cutting portion 221, the second cutting portion 222, and the third cutting portion 223.

The non-cutting portion 224 is located between the first cutting portion 221 and the second cutting portion 222. The non-cutting portion 224 has a smooth outer peripheral surface having a constant outer diameter and no irregularities along the axial direction. The outer diameter of the non-cutting portion 224 may change along the axial direction.

The outer peripheral surface of the third cutting portion 223 has a cut-out portion or groove 225 configured so as to be substantially V-shaped in an axially orthogonal cross section. In the present embodiment, the cut-out portion 225 is provided every 120 degrees in the circumferential direction. Therefore, the structure 220 has three cut-out portions 225 disposed at equal intervals in the circumferential direction. An edge portion 226 of each cut-out portion 225 is formed smoothly with a curvature. The number of cut-out portions or grooves 225 is not limited to three.

The inner ring 270 is rotatably supported by the outer ring 280 provided at a distal portion of the outer sheath 250 via the rolling elements 260. The inner ring 270 is formed with three slits 271 located on the proximal side of the three cut portions 225. The slits 271 extend along the axis X (i.e., the slits 271 are axially extending slits). The inner ring 270 includes three divided support portions 272 (projection portions) that are interposed between the slits 271 and arranged in the circumferential direction. The divided support portions 272 are formed by dividing one tubular body by the slits 271. Each divided support portion 272 is formed with two receiving portions 273 that can accommodate the rolling elements 260. In each receiving portion 273, a spherical rolling element 260 that comes into contact with the inner peripheral surface of the outer ring 280 is rotatably accommodated. An engagement portion 274 that protrudes radially outward is formed at a proximal portion of the divided support portion 272. The engagement portion 274 is rotatably fitted in the engagement concave portion 252 formed on the inner peripheral surface of the outer sheath 250. Therefore, the structure 220 is prevented from moving in the axial direction with respect to the outer sheath 250 and falling off. The outer ring 280 has a raceway surface 281 on the inner peripheral surface on which the rolling elements 260 roll. The raceway surface 281 is formed with two groove portions 282 that support the rolling elements 260 so that they can roll. The groove portion 282 extends in the circumferential direction. The drive shaft 230 is fixed to the inner peripheral surface of the structure 220. The inner ring 270, the outer ring 280, and the rolling elements 260 constitute the bearing 210. The inner ring 270 is integrated with the structure 220 having the cutting portion (i.e., the inner ring 270 is a part of the cutting portion so that rotation of the cutting portion 221, 222, 223 results in rotation of the inner ring 270), but may be separate from the structure 220. Further, the outer ring 280 is separate from the outer sheath 250, but may be integrated with the outer sheath 250.

Although the constituent material of the structure 220 is not particularly limited, for example, stainless steel, CoCr, NiCr, brass, WC, tantalum (Ta), Ti (titanium), Pt (platinum), Au (gold), W (tungsten), polyolefin such as polyethylene and polypropylene, polyester such as polyamide and polyethylene terephthalate, a fluorine-based polymer such as polytetrafluoroethylene (PTFE) and tetrafluoroethylene-ethylene copolymer (ETFE), polyether ether ketone (PEEK), polyimide, or the like can be suitably used.

The maximum outer diameter of the structure 220 can be appropriately selected depending on the inner diameter of the biological lumen to which the structure 220 is applied, and is, for example, 0.5 to 10.0 mm, and can be 2.0 mm as an example.

The drive shaft 230 is formed in a tubular shape, the distal side is fixed to the proximal end portion of the structure 220, and a driven gear 231 is fixed to the proximal side of the drive shaft 230. A proximal portion of the drive shaft 230 is rotatably interlocked with a casing 241 of the operation unit 240.

The drive shaft 230 is flexible and has a property of transmitting rotational power acting from the proximal side or proximal end to the distal side or distal end. The drive shaft 230 is, for example, a single-layer coil, or a multi-layer coil-like pipe body such as a three-layer coil in which the winding direction is alternately set to the right and left and right.

The operation unit 240 includes the casing 241, a drive gear 242 that meshes with the driven gear 231, and a motor 244 that is a drive source including a rotation shaft 243 to which the drive gear 242 is fixed. The operation unit 240 further includes a battery 245 such as a battery that supplies power to the motor 244, and a switch 246 that controls driving of the motor 244. When the switch 246 is turned on, the rotation shaft 243 of the motor 244 and the drive gear 242 rotate. When the drive gear 242 rotates, the driven gear 231 meshing with the drive gear 242 rotates, and the drive shaft 230 rotates.

Next, the operation of the medical device 200 will be described.

When the drive shaft 230 is rotated, the structure 220 interlocked with the drive shaft 230 rotates. When the structure 220 rotates, the rolling elements 260 slide on the sliding surface 275 of the receiving portion 273 and rotate, and also roll in the groove portion 282 of the outer ring 280. Accordingly, this allows the structure 220 to smoothly rotate at the distal portion of the outer sheath 250. The rolling elements 260 may not only roll in the groove portion 282 but may also slide.

Next, a method of using the medical device 200 will be described.

The operator inserts the distal portion including the structure 220 of the medical device 200 into a blood vessel having a stenosed site, for example. Next, when the switch 246 (see FIG. 14) of the operation unit 240 is turned on, the driving force of the motor 244 is transmitted from the drive gear 242 to the driven gear 231. Then, the drive shaft 230 interlocked with the driven gear 231 rotates, and the structure 220 interlocked with the drive shaft 230 rotates. By repeating the advancing and retreating (forward and rearward axial movement) of the rotating structure 220, the stenosed site can be effectively cut by the first cutting portion 221, the second cutting portion 222, and the third cutting portion 223 while suppressing damage to the blood vessel wall by the non-cutting portion 224.

Next, while or after the stenosed site is cut by the structure 220, the plunger of the syringe connected to the proximal side of the outer sheath 250 via a Y connector or the like is pulled. Accordingly, a negative pressure is generated inside the outer sheath 250, and the cut stenosed site can be aspirated into the lumen of the outer sheath 250 through the cut portions 225, the slit 271, and the gap between the inner ring 270 and the outer ring 280. When the aspirated object passes through the gap between the inner ring 270 and the outer ring 280, it can be further crushed by the divided support portions 272 of the rotating inner ring 270. Therefore, the medical device 200 can effectively aspirate an object that passes through the gap between the inner ring 270 and the outer ring 280 of the bearing 210 while crushing it into small pieces by the bearing 210. The gap between the inner ring 270 and the outer ring 280 allows not only the flow of the cut stenosed site but also the flow of various substances such as a drug, a contrast agent, and a physiological salt solution.

As described above, the medical device 200 is a medical device 200 for cutting a stenosed site (object) in a biological lumen, and includes a rotatable drive shaft 230, a cutting portion provided on the distal side of the drive shaft 230 for cutting a stenosed site, an outer tube 251 rotatably accommodating the drive shaft 230, an inner ring 270 fixed to the cutting portion, and an outer ring 280 fixed to the outer tube 251, in which a raceway surface 281 on which the rolling element 260 rolls is provided on the outer ring 280, and a receiving portion 273 for rotatably accommodating the rolling element 260 is provided at a position facing the raceway surface 281 of the inner ring 270.

In the medical device 200 configured as described above, since the inner ring 270 is provided with the receiving portions 273 that each rotatably accommodates one of the rolling elements 260, a retainer for holding the rolling elements 260 is unnecessary. Therefore, a gap that penetrates in the axial direction between the inner ring 270 and the outer ring 280 can be widely secured, and the cut stenosed site can be discharged by using this gap as a flow path. Therefore, the medical device 200 can allow the cut stenosed site to pass through the inside of the bearing 210 and flow, while having the bearing 210. Therefore, the diameter of the medical device 200 can be reduced and the function of circulating the object can be simultaneously realized.

<Application Example of Other Bearing to Medical Device>

Figure 17:
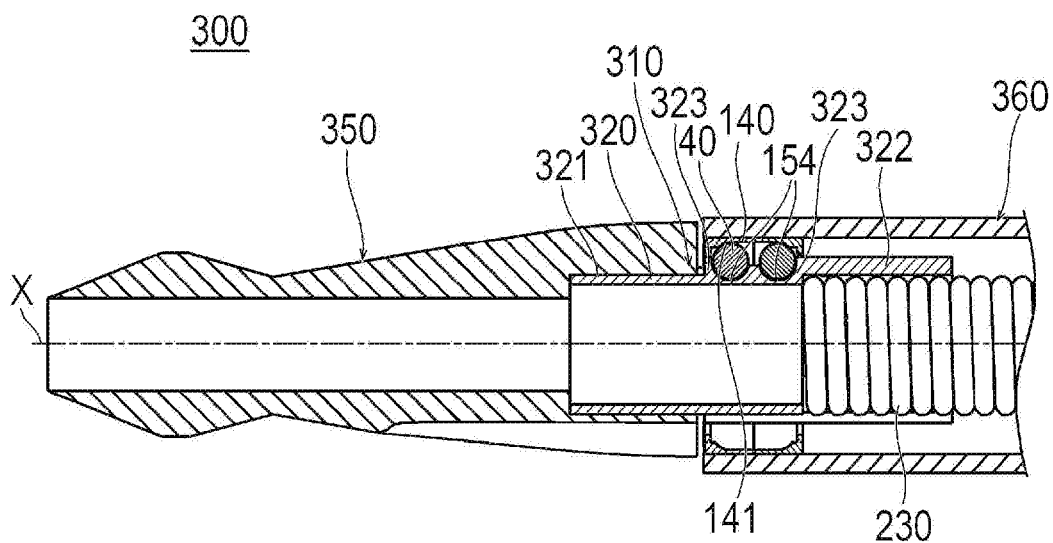
FIG. 17 is a cross-sectional view showing a distal portion of another medical device.
Figure 18:
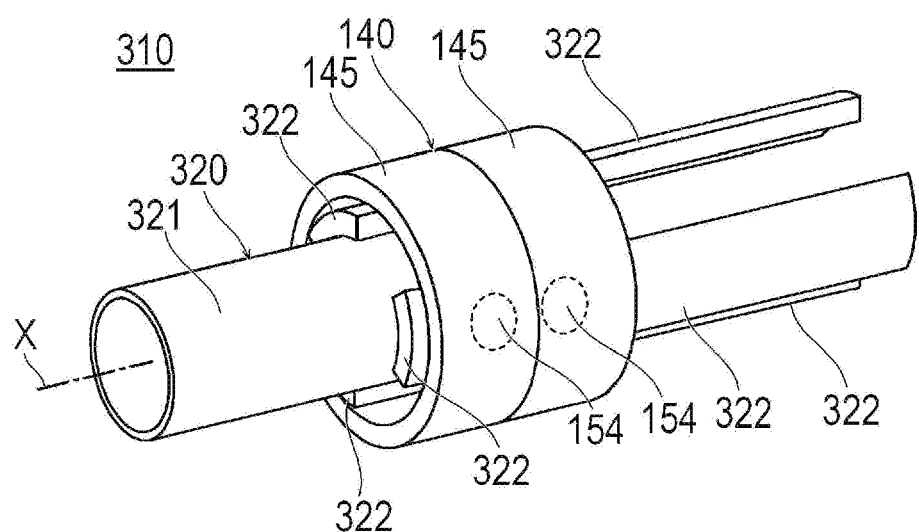
FIG. 18 is a perspective view showing a bearing of another medical device.

A medical device 300 has a bearing 310 as shown in FIGS. 17 and 18. The bearing 310 differs from the bearing 130 (see FIG. 11) according to the fifth embodiment only in the shape of an inner ring 320. Parts in this embodiment having functions the same or similar as those in the above-described embodiments are identified by the same reference numerals and a detailed description of such parts is not repeated.

The inner ring 320 of the bearing 310 includes a cylindrical inner ring main body 321 and three projection portions 322 protruding radially outward from the inner ring main body 321. The inner ring main body 321 has a cylindrical shape that protrudes longer to one side in the axial direction than the position where the outer ring 140 is disposed with respect to the inner ring 320. Each projection portion 322 extends axially longer than the position where the outer ring 140 is disposed with respect to the inner ring 320, in a direction opposite to the direction in which the inner ring main body 321 protrudes in the axial direction. Each projection portion 322 has two receiving portions 323 on which two concave sliding surfaces 154 are formed. The projection portions 322 of the inner ring 320 are interlocked with the drive shaft 230. The inner ring main body 321 is interlocked with a structure 350 having a cutting portion. The outer ring 140 is fixed to an outer sheath 360.

Next, the operation of the medical device 300 will be described.

When the drive shaft 230 is rotated, the inner ring 320 interlocked with the drive shaft 230 rotates, and the structure 350 interlocked with the inner ring 320 rotates. When the inner ring 320 rotates, the rolling elements 40 slide on the sliding surface 154 of the projection portion 322 and rotate, and also roll on the raceway surface 141 of the outer ring 140. Accordingly, this allows the structure 350 to rotate smoothly at the distal portion of the outer sheath 360.

As described above, in the medical device 300, the inner ring main body 321 of the bearing 310 protrudes to one side in the axial direction from the position where the outer ring 140 is disposed with respect to the inner ring 320. Therefore, it is easy to connect the inner ring main body 321 to the structure 350 without interference from the outer ring 140.

Further, the projection portions 322 of the bearing 310 protrudes from the position where the outer ring 140 is disposed with respect to the inner ring 320, to the axial side opposite to the side where the inner ring main body 321 protrudes in the axial direction. Therefore, it is easy to connect the projection portion 322 to the drive shaft 230 without interference from the outer ring 140 and the inner ring main body 321.

The present invention is not limited to only the above-described embodiments, and various modifications can be made by those skilled in the art within the technical idea of the present invention. For example, the biological lumen into which the medical device is inserted is not limited to a blood vessel, and may be, for example, a vessel, a ureter, a bile duct, a fallopian tube, a hepatic duct, or the like. Further, the bearings according to the first to seventh embodiments can be applied to a medical device like the medical device described above. The bearings according to the first to seventh embodiments may be applied to a medical device not intended for cutting or a device not intended for medical treatment. Further, each of the above-described configurations can be used in appropriate combination.

In addition, the receiving portion in the above-described embodiment is a part of the inner ring or the outer ring, but may be a member separate from the inner ring or the outer ring, and may be fixed to the inner ring or the outer ring.

Further, the depth of the sliding surface formed in the receiving portion for accommodating the rolling element of the above-described embodiments may be different depending on the receiving portion. Accordingly, the axis of the inner ring does not coincide with the axis of the outer ring. Therefore, for example, when this bearing is applied to the medical devices 200 and 300 shown in FIGS. 15 and 17, the axes of the structures 220 and 350 having a cutting function do not match the axes of the outer sheaths 250 and 360. Therefore, when the structures 220 and 350 rotate, the axes of the structures 220 and 350 rotate around the axes of the outer sheaths 250 and 360, and the structures 220 and 350 swing. Accordingly, the cutting range by the structures 220 and 350 can be expanded. The difference between the maximum value and the minimum value of the depth of the plurality of sliding surfaces provided in one bearing is not particularly limited, but is, for example, 1 to 199 μm. More preferably, the difference is 10 to 190 μm. The difference in depth described above is to prevent the inner and outer rings of the bearing from contacting each other. For example, this is a value when the radial distance between the inner and outer rings in the radial direction is 100 μm when the inner ring and the outer ring are arranged coaxially. Further, the plurality of receiving portions that accommodate the rolling elements do not have to be disposed at equal intervals in the circumferential direction.

The detailed description above describes embodiments of a bearing, medical device, and manner of use/operation representing examples of the inventive bearing, medical device, and manner of use/operation disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

REFERENCE SIGNS LIST 10, 50, 70, 100, 130, 160, 180, 210, 310 bearing
20, 60, 80, 130, 150, 270, 320 inner ring
21, 191, 321 inner ring main body
22, 81, 151, 322 projection portion
23, 35, 61, 83, 111, 152, 273, 323 receiving portion
24, 113, 154, 275 sliding surface
27, 31, 124, 141, 281 raceway surface
29, 112, 153 inner ring wall portion (first wall portion)
30, 120, 140, 170, 190, 280 outer ring
32, 121, 142, 282 groove portion
37, 122, 143, 144 outer ring wall portion (second wall portion)
40, 260 rolling element
41 first rolling element
42 second rolling element
62 flow hole
82 slope
171, 191 cutting projection portion
200, 300 medical device
220, 350 structure
221 first cutting portion
222 second cutting portion
223 third cutting portion
224 non-cutting portion
251 outer tube
X axis

What is claimed is:

1. A medical device for cutting an object in a biological lumen, the medical device comprising:
   a rotatable drive shaft;
   a cutting portion configured to be positioned in the biological lumen, the cutting portion being on a distal side of the drive shaft and being rotatable together with the drive shaft so that rotation of the drive shaft rotates the cutting portion to cut the object in the biological lumen;
   an outer tube rotatably accommodating the drive shaft;
   an inner ring disposed on a cutting portion side;
   an outer ring disposed on an outer tube side;
   a plurality of rolling elements positioned between the inner ring and the outer ring;
   one of the inner ring or the outer ring including a raceway surface on which the rolling elements roll, the other of the inner ring or the outer ring including a facing surface that faces the raceway surface;
   a plurality of receiving portions individually rotatably accommodating the rolling elements, the plurality of receiving portions being provided on a side of the inner ring or the outer ring facing the raceway surface; and
   a radial distance between the raceway surface and the facing surface at locations circumferentially between the receiving portions being greater than the radial distance between the raceway surface and the facing surface at the receiving portions so that axially extending gaps exist between the inner ring and the outer ring, the gaps defining axially extending flow paths that allow a fluid or an object to flow through the axially extending gaps during operation of the medical device.

2. The medical device according to claim 1, wherein the inner ring is fixed to the cutting portion so that rotation of the cutting portion results in rotation of the inner ring.

3. The medical device according to claim 1, wherein the inner ring includes a plurality of axially extending and circumferentially spaced-apart slits that define a plurality of circumferentially spaced-apart support portions, each support portion being located between two of the slits, each support portion including a plurality of the receiving portions.

4. The medical device according to claim 1, wherein the outer ring is fixed to a distal end of the outer tube.

5. The medical device according to claim 1, wherein the inner ring includes a cylindrically-shaped and axially extending inner ring main body that protrudes distally beyond a distal end of the outer ring, the inner ring also including three circumferentially spaced-apart and axially extending projection portions that protrude proximally beyond a proximal end of the outer ring, each projection portion including a plurality of the receiving portions each of which includes a concave sliding surface.

6. A bearing having opposite axial ends, the bearing comprising:
   an inner ring that includes an axially extending through hole;
   an outer ring that includes an axially extending through hole;
   a plurality of rolling elements between the inner ring and the outer ring;
   one of the inner ring or the outer ring including a raceway surface in contact with the rolling elements and on which the rolling elements roll, the other of the inner ring or the outer ring including a facing surface that faces the raceway surface;

a plurality of receiving portions each rotatably accommodating one of the rolling elements, the receiving portions being provided on a side of the inner ring or the outer ring facing the raceway surface;

a plurality of circumferentially spaced-apart gaps each located between the inner ring and the outer ring and each positioned between circumferentially adjacent ones of the rolling elements, each of the gaps extending axially between the opposite axial ends of the bearing and being open at opposite axial ends of the gap to define a flow path that allows a fluid or an object to flow through the axially extending gaps; and a radial distance between the raceway surface and the facing surface in the axially extending gaps being greater than the radial distance between the raceway surface and the facing surface at the receiving portions.

7. The bearing according to claim 6, wherein the receiving apportions are convex-shaped receiving portions that protrude toward the raceway surface.

8. The bearing according to claim 7, wherein the inner ring and the outer ring are relatively rotatable about a rotation axis of the bearing, the convex receiving portion has, on a side surface on a rotation direction side, a slope inclined with respect to the rotation axis.

9. The bearing according to claim 7, wherein a cutting projection portion protruding toward the convex-shaped receiving portion is provided on a side of the inner ring or the outer ring facing the convex-shaped receiving portion.

10. The bearing according to claim 6, wherein a friction coefficient of a sliding surface of the receiving portion in contact with the rolling elements is smaller than a friction coefficient of the raceway surface.

11. The bearing according to claim 6, wherein the receiving portion includes a sliding surface in contact with the rolling elements, the sliding surface of the receiving portion being made of a material different from a material of which the raceway surface is made.

12. The bearing according to claim 6, wherein the receiving portion includes a sliding surface in contact with the rolling elements, the sliding surface of the receiving portion having a surface microstructure different from a surface microstructure of the raceway surface.

13. The bearing according to claim 6, wherein the receiving portion includes a sliding surface in contact with the rolling elements, the receiving portion including a through hole through which a lubricating fluid flows to the sliding surface of the receiving portion in contact with the rolling element.

14. The bearing according to claim 6, wherein the receiving portion has a first wall portion located on a first axial side of the bearing with respect to the rolling elements, the raceway surface has a second wall portion located on a second axial side of the bearing with respect to the rolling elements, the first and second axial sides being opposite axial sides of the bearing, and the rolling elements being interposed and supported in the axial direction between the first wall portion and the second wall portion.

15. The bearing according to claim 14, wherein the inner ring and the outer ring are relatively rotatable about a rotation axis of the bearing;

the receiving portion including a further wall portion located on the second axial side of the bearing, the raceway surface including an additional wall portion located on the first axial side of the bearing;

the first wall portion and the further wall portion terminating at respective ends, a perpendicular distance between the end of the first wall portion and the rotation axis being greater than the perpendicular distance between the end of the further wall portion and the rotation axis, and the second wall portion and the additional wall portion terminating at respective ends, a perpendicular distance between the end of the second wall portion and the rotation axis being less than the perpendicular distance between the end of the additional wall portion and the rotation axis.

16. A bearing having opposite axial ends, the bearing comprising:

a first ring that includes an axially extending through hole;

a second ring that includes an axially extending through hole;

a plurality of spherical rolling elements positioned between the first ring and the second ring;

the first ring including a plurality of circumferentially spaced-apart projections that project toward the second ring relative to the portions of the first ring adjacent the projections;

each of the projections including a convex-shaped receiving portion at which is positioned one of the spherical rolling elements;

the second ring including a raceway surface in contact with the rolling elements and on which the rolling elements roll;

the first ring including a facing surface that faces the raceway surface;

the first ring and the second ring being relatively rotatable about a rotation axis of the bearing;

one of the first ring and the second ring being an inner ring of the bearing, and the other of the first ring and the second ring being an outer ring of the bearing; and a plurality of circumferentially spaced-apart gaps each located between the first ring and the second ring and each positioned between circumferentially adjacent ones of the rolling elements, each of the gaps extending axially between the opposite axial ends of the bearing and being open at opposite axial ends of the gap to define a flow path that allows a fluid or an object to flow through the axially extending gaps; and a radial distance between the raceway surface and the facing surface in the axially extending gaps being greater than the radial distance between the raceway surface and the facing surface at the receiving portions.

17. The bearing according to claim 16, further comprising a cutting projection portion on the second ring that projects toward the convex-shaped receiving portions of the first ring.

18. The bearing according to claim 16, wherein the convex-shaped receiving portions each include a sliding surface possessing a friction coefficient smaller than a friction coefficient of the raceway surface.

19. The bearing according to claim 16, wherein the first ring has a first wall portion located on a first axial side of the bearing with respect to the rolling elements, the second ring includes a second wall portion located on a second axial side of the bearing with respect to the rolling elements, the first and second axial sides being opposite axial sides of the bearing, and the rolling elements being interposed and supported in the axial direction between the first wall portion and the second wall portion.

20. The bearing according to claim 19, wherein the first ring includes a further wall portion located on the second axial side of the bearing, and the second ring includes an additional wall portion located on the first axial side of the bearing;

the first wall portion and the further wall portion terminating at respective ends, a perpendicular distance between the end of the first wall portion and the rotation axis being greater than the perpendicular distance between the end of the further wall portion and the rotation axis, and the second wall portion and the additional wall portion terminating at respective ends, a perpendicular distance between the end of the second wall portion and the rotation axis being less than the perpendicular distance between the end of the additional wall portion and the rotation axis.

* * * * *